United States Patent [19]

Haber et al.

[11] Patent Number: 5,226,894

[45] Date of Patent: Jul. 13, 1993

[54] SAFETY SYRINGE ASSEMBLY WITH RADIALLY DEFORMABLE BODY

[75] Inventors: Terry M. Haber, Lake Forest; William H. Smedley, Lake Elsinore; Clark B. Foster, Laguna Niguel; John A. Lewis, Costa Mesa, all of Calif.

[73] Assignee: Sterling Winthrop Inc., New York, N.Y.

[21] Appl. No.: 580,931

[22] Filed: Sep. 11, 1990

[51] Int. Cl.⁵ .............................................. A61M 5/32
[52] U.S. Cl. ...................................... 604/198; 604/240
[58] Field of Search ............... 604/110, 192, 197, 198, 604/263, 240

[56] References Cited

U.S. PATENT DOCUMENTS

| | | |
|---|---|---|
| 2,571,653 | 10/1951 | Bastien . |
| 4,356,822 | 11/1982 | Winstead-Hall ............... 604/198 X |
| 4,367,738 | 1/1983 | Legendre et al. . |
| 4,592,744 | 6/1986 | Jagger et al. . |
| 4,655,751 | 4/1987 | Harbaugh ............... 604/198 |
| 4,752,290 | 6/1988 | Schramm ............... 604/198 |
| 4,758,230 | 7/1988 | Rycroft ............... 604/198 |
| 4,834,717 | 5/1989 | Haber et al. . |
| 4,871,355 | 10/1989 | Kikkawa . |
| 4,874,383 | 10/1989 | McNaughton ............... 604/198 |
| 4,900,311 | 2/1990 | Stern et al. ............... 604/198 |
| 4,927,417 | 5/1990 | Moncada et al. ............... 604/198 |
| 4,935,016 | 6/1990 | Deleo ............... 604/198 |
| 4,991,601 | 2/1991 | Kasai et al. ............... 128/763 |
| 5,013,302 | 5/1991 | Schmidt ............... 604/198 |
| 5,059,185 | 10/1991 | Ryan ............... 604/198 |
| 5,067,945 | 11/1991 | Ryan et al. ............... 604/198 |

Primary Examiner—John D. Yasko
Assistant Examiner—Adam J. Cermak
Attorney, Agent, or Firm—William J. Davis

[57] ABSTRACT

The present invention is directed to a syringe assembly (48), particularly useful for use with conventional prefilled pharmaceutical cartridge-needle units (46), including a hollow body (4) housing the cartridge-needle unit or other syringe structure. The substantially hollow body and the syringe structure include mating slits (28, 29, 30) and a ring (26) so that the needle (60) can be exposed for I.M. injection use and then withdrawn into the body for safety. The body is configured so that when the user diametrically squeezes the body adjacent the slit(s), the ring disengages the slit(s) due to the deformation of the body which permits the needle tip (62) to be positioned inside, for safety, or outside, for use, of the body. The internal position is also useful for safely injecting a pharmaceutical into an IV port (88). When the invention is used with a conventional pharmaceutical cartridge-needle unit as the syringe structure, the body can be part of an enclosure unit (2) which acts as the packaging for the pharmaceutical cartridge-needle unit, as the body of the syringe for administration of I.V. and I.M. injections, and as individual integral sharps containment for safe antineedle-stick disposal of the used cartridge-needle unit.

35 Claims, 9 Drawing Sheets

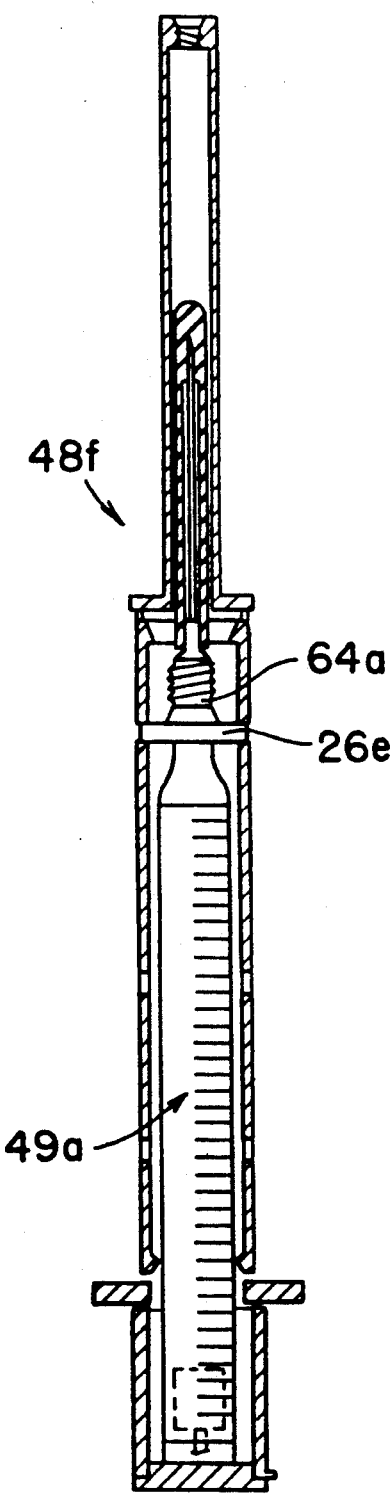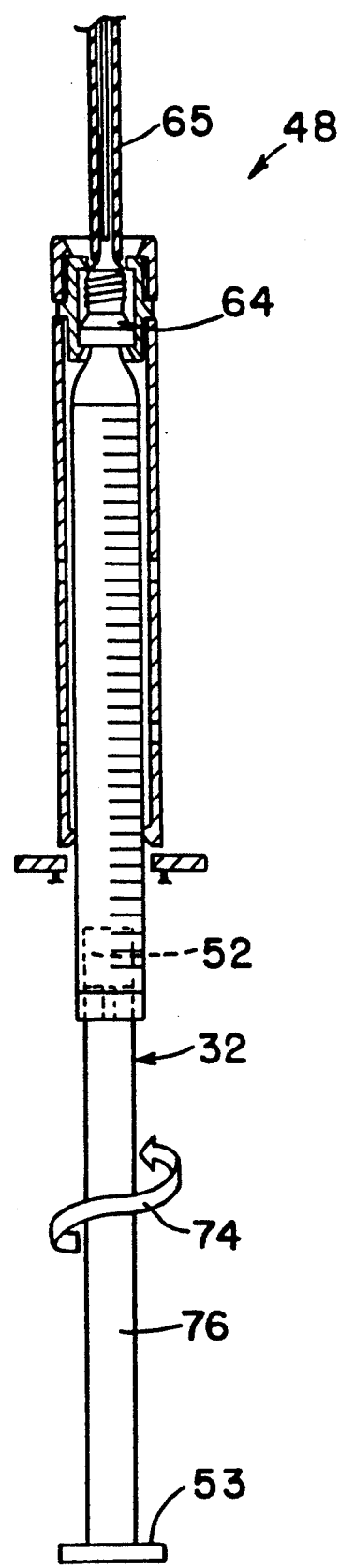

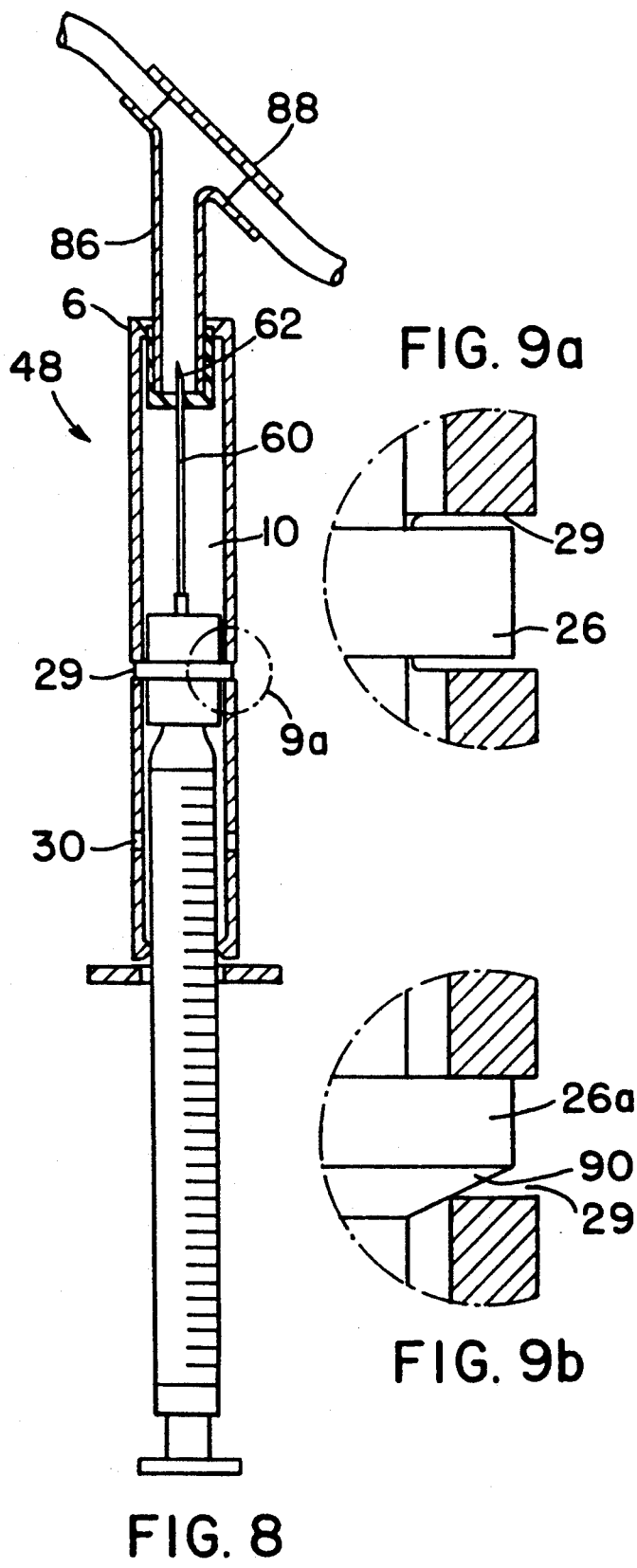
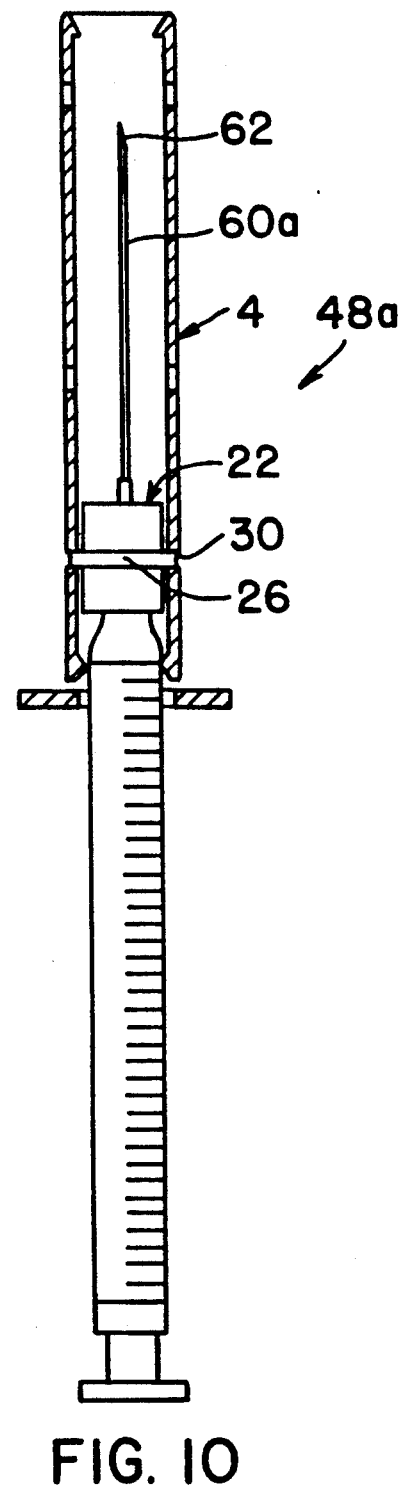
FIG. 8  FIG. 9a  FIG. 9b  FIG. 10

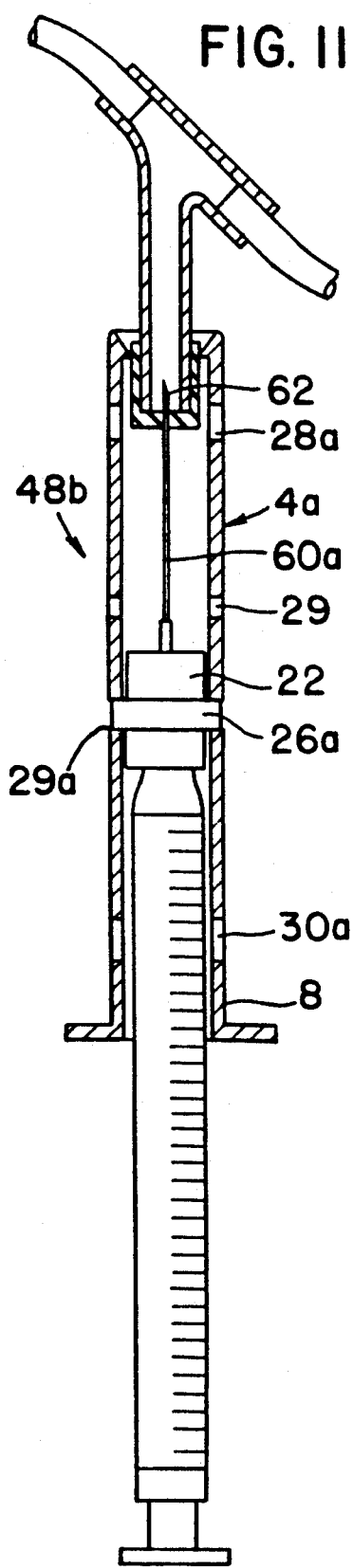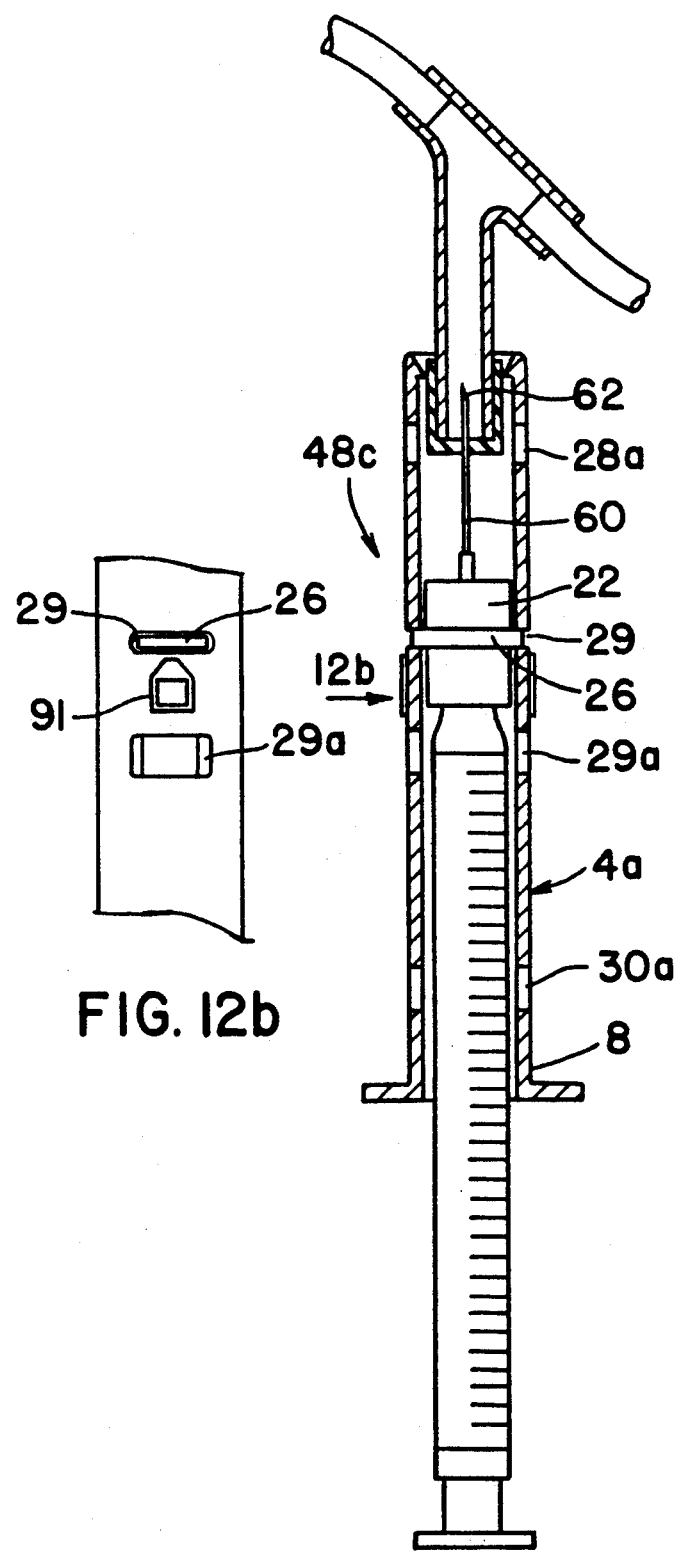
FIG. 11
FIG. 12b
FIG. 12a

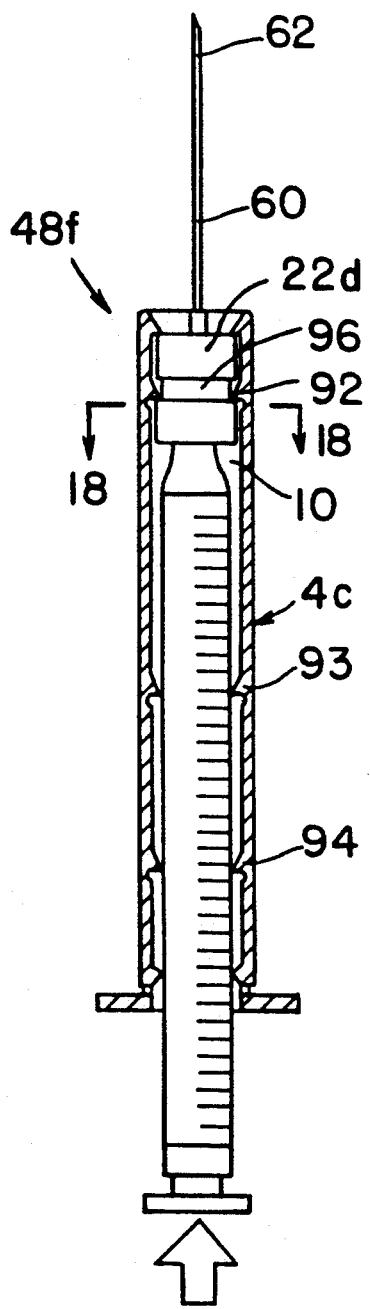
FIG. 17
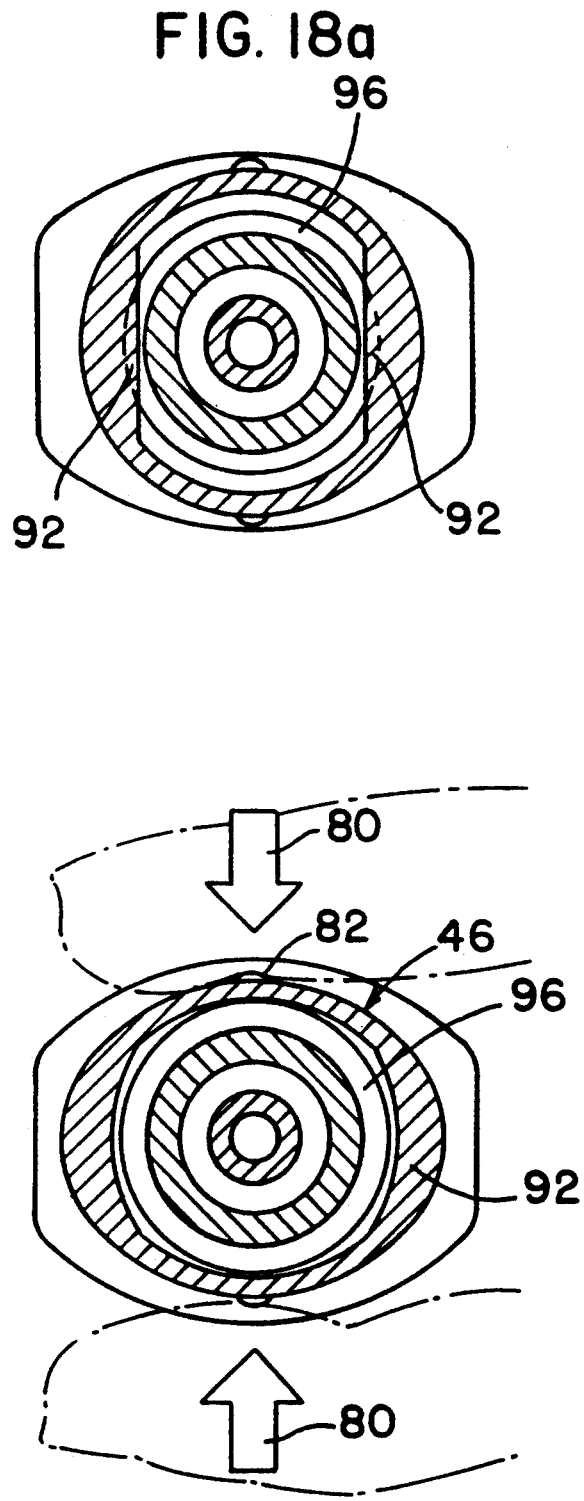
FIG. 18a
FIG. 18b

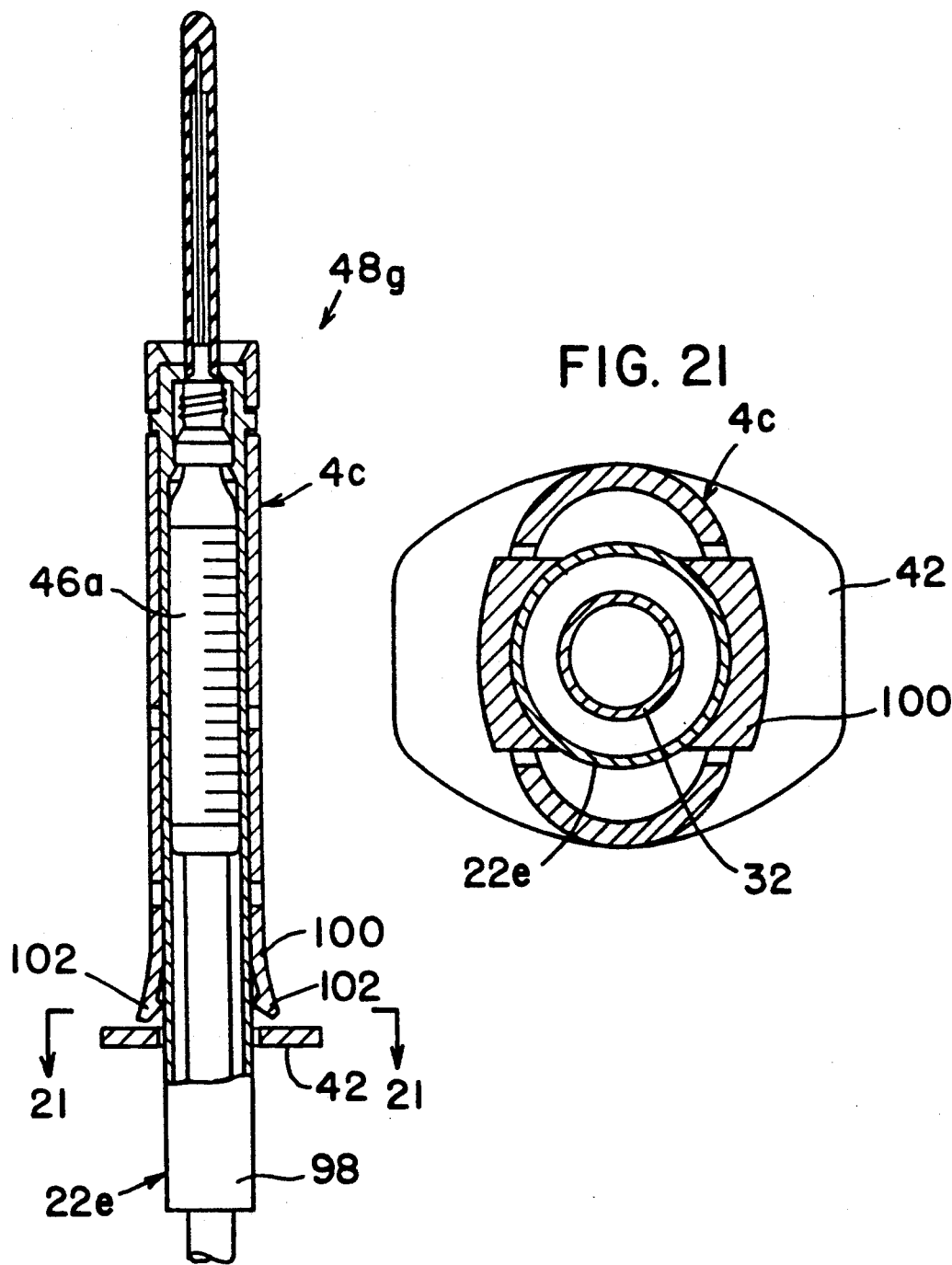

SAFETY SYRINGE ASSEMBLY WITH RADIALLY DEFORMABLE BODY

CROSS REFERENCE TO RELATED APPLICATION

This application is related to U.S. patent application Ser. No. 07/558,878, filed Jul. 27, 1990, the disclosure of which is incorporated by reference.

BACKGROUND OF THE INVENTION

The need for preventing inadvertent needle sticks has been recognized for many years. For example, U.S. Pat. No. 2,571,653 to Bastien shows a syringe in which the barrel of the syringe is mounted within a protective sheath. The sheath can be placed at different axial positions relative to the barrel, one exposing the needle for use and one covering the needle for safety. Many other safety syringe assemblies have been developed as well. However, one of the problems with the prior art safety syringe assemblies is that they generally cannot be used with conventional syringes, are awkward to use and make calibrations and volume graduations difficult to see clearly. Also, existing safety syringe assemblies often are to economical to produce; this is especially true when the syringe structures are intended to be disposable.

SUMMARY OF THE INVENTION

The present invention is directed to a syringe assembly, particularly useful for use with conventional prefilled pharmaceutical cartridge-needle units, including a hollow body housing the cartridge-needle unit or other syringe structure. The hollow body and the syringe structure include mating positioning elements to permit the syringe structure to be secured at one or more axial positions within the body. The positioning elements are preferably radially extending recesses and extensions. The hollow body typically has at least two internal recesses sized and positioned to negate a radially extending member carried by the syringe structure so that the needle can be partially or totally exposed for use and then withdrawn into the body for safety. The body is configured so that when the user squeezes the body at positions diametrically adjacent the recess, the radially extending member becomes disengaged rom the recess due to the deformation of the body. This frees the needle permitting it to be repositioned within the body.

The body is constructed so that the body may be deformed to permit the radially extending member to freely move from the recess to permit the syringe structure and body to move axially relative to one another. This may be achieved by constructing the body with an elliptical cross-sectional shape and forming pairs of the recess through the walls of the body while constructing the radially extending member as an annular, outwardly extending syringe carried by the syringe structure. The radially extending member can be disengaged from the recesses by squeezing the body to deform the body from the generally elliptical shape to a generally circular shape. Preferably, three sets (or four sets to permit one molded body to accommodate both short and long needle lengths) of axially spaced-apart recesses are provided. One recess near the distal end of the body for I.M. (IntraMuscular) injections. An intermediate recess (or two to accommodate both long and short needle canhnula) such that the tip of the needle is within the interior of the body may be used for safer disposal. Also, this position may be used for I.V. (IntraVenous) port injection. By properly sizing the opening at the distal end of the body, the body may be placed over the injection valve of an I.V. port, permitting the sharpened point of the needle canula to pierce the membrane port only after this sharpened point has been shielded from human contact. This permits I.V. port injection with a high degree of safety and efficacy. The recess or recesses closest to the plunger end of the body are used to ensure the needle tip is well within the body for safe disposal of the syringe structures.

One of the primary advantages of the invention is that it permits the needle of a syringe structure to be safely housed within the body in an extremely simple and cost effective manner. In addition, although the invention can be used with conventional syringes, the invention finds particular utility when used with prefilled pharmaceutical cartridge-needle units. In such case, the body can be part of an enclosure unit, the enclosure unit acting as both the protective packaging for the cartridge-needle unit, and also as a part of the operational syringe assembly itself.

Other features and advantages will appear from the following description in which the preferred embodiments have been set forth in detail in conjunction with the accompanying drawings.

BRIEF DESCRIPTION OF THE DRAWINGS

FIG. 5 illustrates the syringe assembly of FIG. 4 after the end unit has been separated from the body section and discarded and the stem section has been separated from the adapter and mounted to the piston at the plunger end of the barrel of the cartridge-needle unit;

FIG. 8 illustrates the movement of the cartridge-needle unit from the use position of FIG. 6, with the needle exposed, to the safe position of FIG. 8, with the needle fully housed within the body section, and also illustrates how the syringe assembly of FIGS. 6 and 8 could be used to inject a medicine into, or remove a sample from, an injection arm of an IV port while keeping the sharpened tip of the needle in a safe position;

FIG. 9A is an enlarged view taken along line 9A of FIG. 8 illustrating the engagement of a standard adapter ring within a body slot;

FIG. 9B shows an alternative embodiment of the adapter ring of FIG. 9A in which the plunger facing surface of the ring provides a ramp effect to enhance movement of the cartridge-needle unit towards the plunger end of the body section;

FIG. 10 illustrates the syringe assembly of FIG. 6 in which the adapter ring is positioned within the body sots adjacent the plunger end of the body section to accommodate longer needles than used with the embodiment of FIG. 8;

FIGS. 11 and 12a illustrate alternative embodiments of the syringe structure of FIG. 8 adapter for use with different length needles and including different width body slots to accommodate different width adapter rings so the same body section can be used with needles of different lengths and still maintain the proper position of the tip of the needle for IV port use;

FIG. 12b is a partial side view of the syringe structure of FIG. 12a;

FIG. 17 illustrates a further embodiment of the invention in which the outer surface of the body section is normally cylindrical with the inner surface having internal flanges which engage a circumferential slot formed in an adapter mounted to the hub of the cartridge-needle unit;

FIG. 18A is a cross-sectional view of the syringe assembly of FIG. 17 taken along line 18—18 illustrating the engagement of the flanges into the annular slot;

FIG. 18B illustrates the syringe assembly of FIG. 18A after the body section has been deformed causing the flanges to disengage from the annular slot to permit the cartridge-needle unit to move axially within the body section;

FIG. 19 illustrates an alternative embodiment of the invention in which the syringe assembly of FIG. 4 has been modified to eliminate the need for a separate adapter by using a cartridge-needle unit in which the hub of the cartridge-needle unit is modified to include its own adapter ring;

FIG. 20 shows a further embodiment of the invention for use with smaller sized cartridge-needle units; and FIG. 21 is a cross-sectional view taken along line 21—21 of FIG. 20.

DETAILED DESCRIPTION OF THE PREFERRED EMBODIMENT

Figure 1:
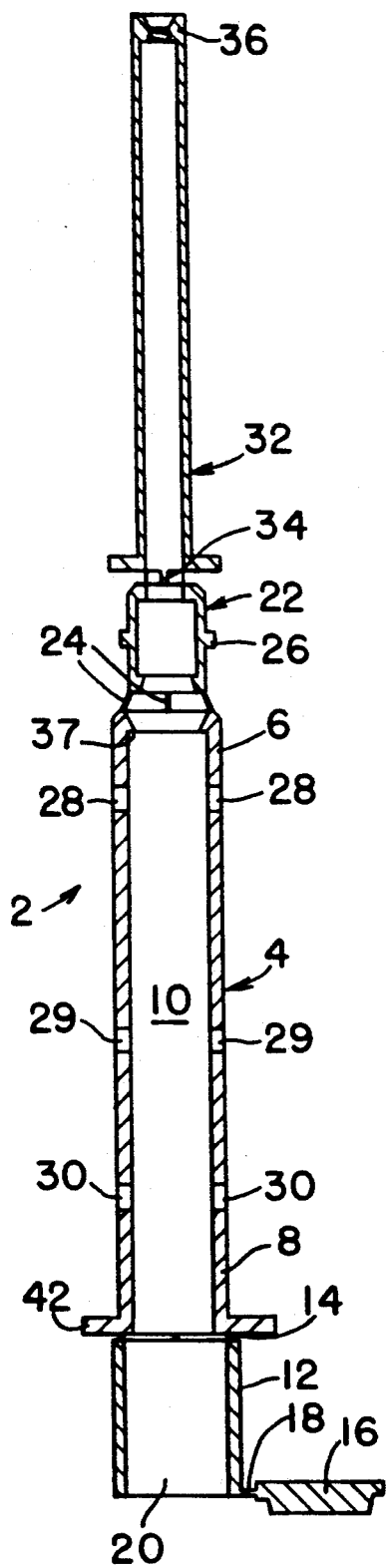
FIG. 1 is a side cross-sectional view of an enclosure unit made according o the invention.

FIG. 1 illustrates a one-piece molded enclosure unit 2, preferably made from clear polypropylene or polyethylene. Enclosure unit 2 includes elongate, substantially hollow body section 4 having a needle end 6, a plunger end 8 and defining an interior 10 therein. Unit 2 also includes an end section 12 frangible connected to plunger end 8 at fragile connections 14. End section 12 includes a cap 16 connected to the remainder of end section 12 by an integral hinge 18 to permit the end 20 of end section 12 to be oriented and sealed as suggested in FIG. 4.

Figure 3:
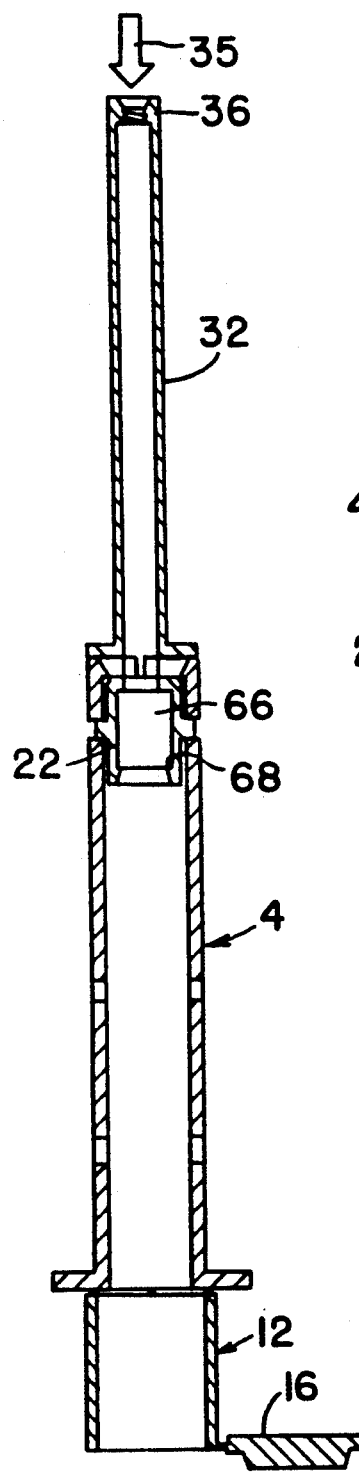
FIG. 3 shows the enclosure unit of FIG. 1 after the adapter has been driven into the body section at the needle end of the body section.

Enclosure unit 2 also included an adapter 22 extending from needle end 6 and attached thereto by frangible connections 24. Adapter 22 has a circumferentially extending adapter ring 26 sized to engage specially positioned paris of body slots 28, 29, 30 formed in body section 4. The method and purpose for doing so will be discussed below. Finally, enclosure unit 2 also includes a hollow stem section 32 franbigly attached to adapter 22 by frangible connections 34. Stem section 32 is hollow to accommodate a sheated (typically sterile) needle (see FIG. 4) and also has a threaded tip 36 to permit stem section 32, once removed from adapter 22, to be secured to a piston to create a plunger as suggested in FIG. 5. Adapter 22 is moved from the position of FIG. 1 to that of FIG. 3 by forcing stem section 32 in the direction of arrow 35, thus severing frangible connections 24, until ring 26 engages slots 28. Body section 4 includes a shoulder 37 at needle end 6. Shoulder 37 helps to keep adapter 22 from inadvertently passing back out of interior 10. Shoulder 37 may be a continuous shoulder, or it may be formed as diametrically opposed segments.

Figure 2:
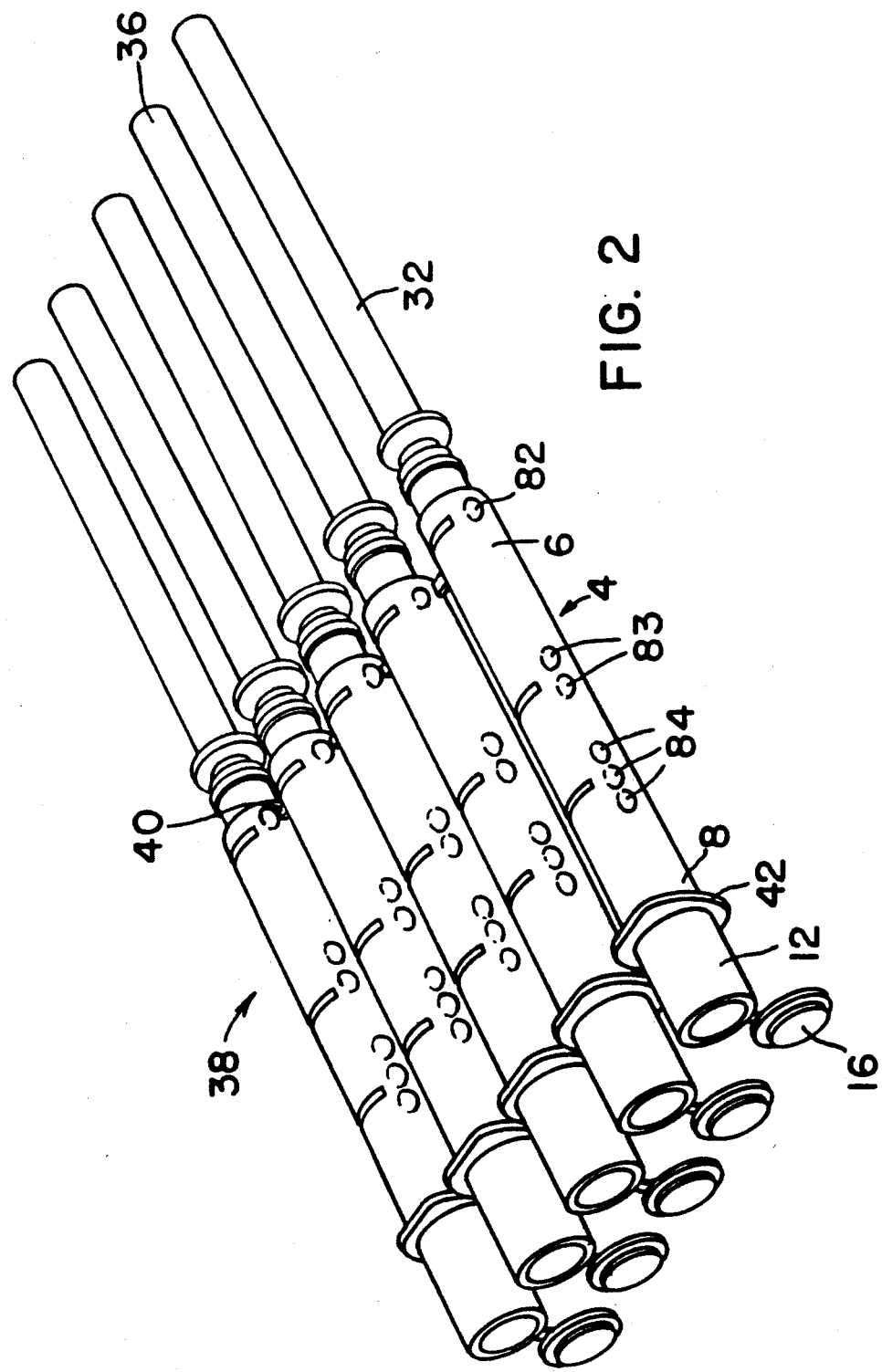
FIG. 2 is an isometric view of a set of the enclosure units of FIG. 1.

FIG. 2 illustrates a set 38 of enclosure units 2 molded as a one-piece item and secured to one another through frangible connections 40 at needle end 6 of body section 4 and by frangible connections (not shown) extending between the finger grips 42 at plunger ends 8. As discussed in the above-referenced application, set 38 of enclosure units 2 acts as both the protective shipping and storage container for cartridge-needle units 46, shown in FIG. 4, as well as providing other functions as discussed below.

Figure 4:
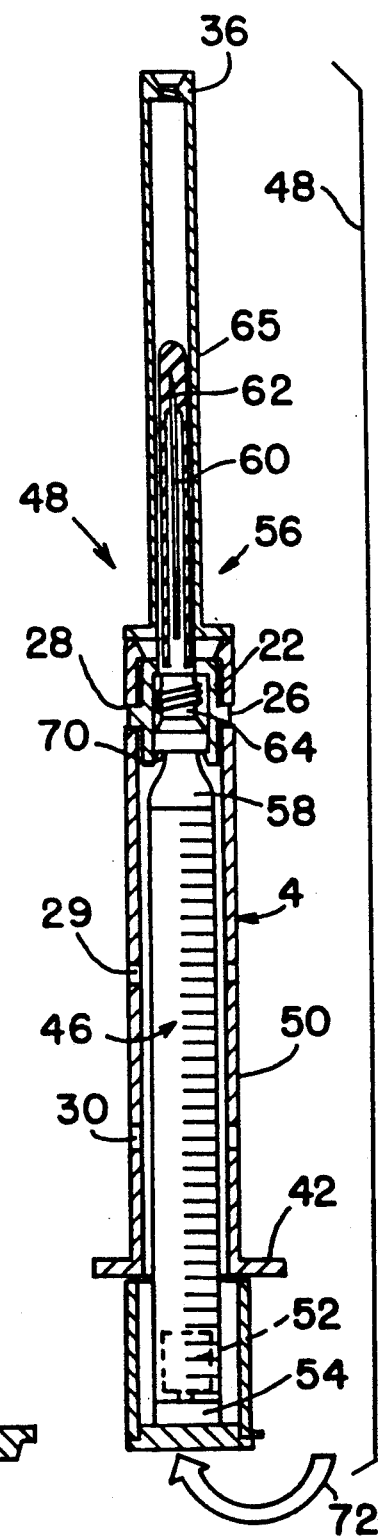
FIG. 4 illustrates a syringe assembly made according to the invention by mounting a cartridge-needle unit mounted within the body section of the enclosure unit of FIG. 3 with the cap at the end section used to plug the end section to maintain the cartridge-needle unit within the enclosure unit and help prevent tampering.

FIG. 4 illustrates enclosure unit 2 with a conventional cartridge-needle unit 46, such as one made by Wyeth-Ayerst Laboratories of Radnor, PA, under the trademark TUBEX, mounted therein to create a syringe assembly 48 in its as-shipped condition. Cartridge-needle unit 46 is of the type including a barrel 50 containing a flowable material, typically a liquid, and having a piston 52, typically initially at the plunger end 54 of barrel 50. A needle assembly 56 is mounted to the needle end 58 of barrel 50. Needle assembly 56 includes a needle 60, having a sharpened tip 62, and a hub 64 used to mount needle 62 barrel 50. An elastomeric sheath 65 is used to cover needle 60 and seal tip 62. Hub 64 is secured within the interior 66 of adapter 22 through the engagement of a lip 68 (see FIG. 3) with the plunger facing edge 70 of hub 64. As suggested by arrow 72, once cartridge-needle unit 46 is mounted within enclosure unit 2, cap 16 is pivoted to close end 20 and is sealed in place, such as with an irreversible mechanical lock which is also tamper-resistant and tamper-evident, an adhesive or with heat or ultrasonic welding techniques. The thickness of cap 16 is sufficient to resist tampering with the contents of barrel 50 while syringe assembly 48 is in its as-shipped condition of FIG. 4. To further inhibit tampering, an internal metal whiled could be used.

Figure 6:
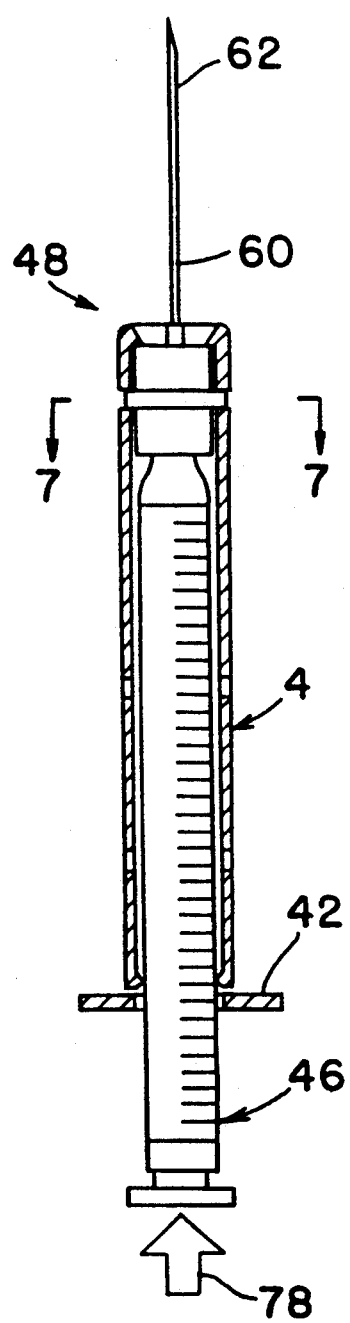
FIG. 6 illustrates the syringe assembly of FIG. 5 after the sheath has been removed from the needle and the plunger has been depressed, injecting the contents of the barrel through the needle.

To use syringe assembly 48, stem section 32 is fractured from adapter 22, typically with a twisting action, and tip 36 is secured to piston 52, typically with a threading action as suggested by arrow 74 in FIG. 5. Next, sheath 64 is removed and the in section is given by driving plunger 76, made up of stem 32, piston 52 and thumb plate 53, as shown by arrow 78 of FIG. 6.

Figure 7A:
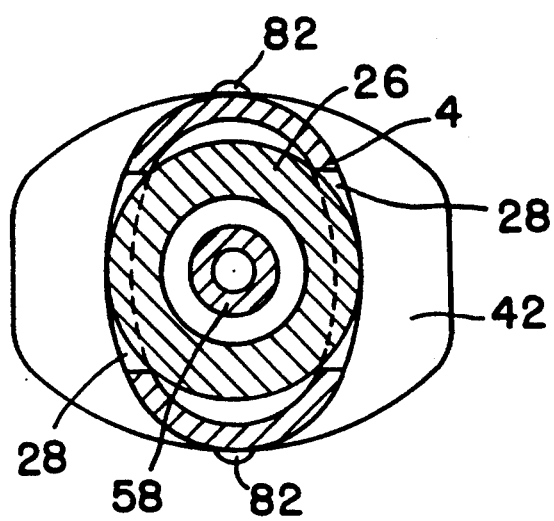
FIG. 7A is a cross-sectional view taken along line 7—7 of FIG. 6 showing the elliptical cross-sectional shape of the body section and the engagement of the adapter ring with the circumferential extending body slots formed in the body section at the needle end of the body section.
Figure 7B:
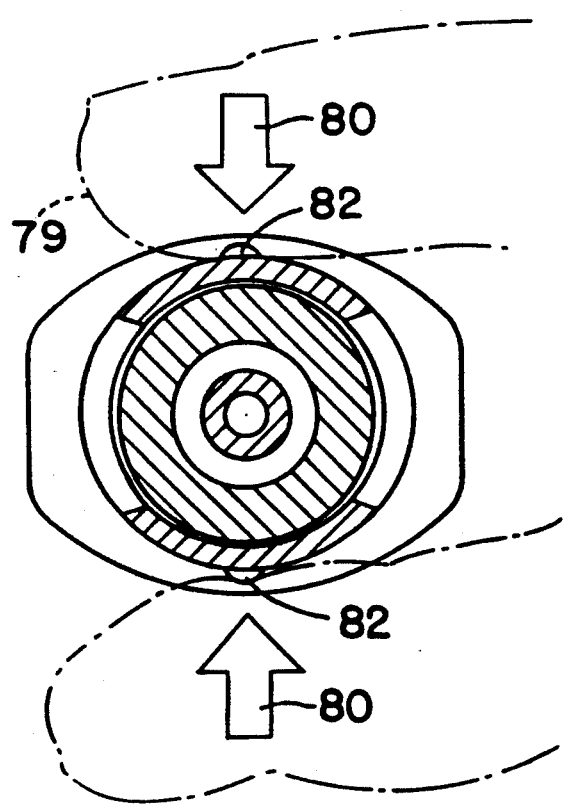
FIG. 7B illustrates the syringe assembly of FIG. 7A after the user has deformed the body section by squeezing the body section as indicated to disengage the adapter ring from the body slots to permit the cartridge-needle unit to be moved axially within the body section.

The present invention permits needle 60 to be withdrawn back into body section 4 in a simple, straightforward manner. As shown in FIG. 7A, body section 4 has an elliptical cross-sectional shape with body slots 28 positioned through the walls of body 4. This permits the outer circumference of adapter ring 26 to enter body slots 28 so long as body section 4 is in its normal, typically undeformed condition of FIG. 7A. To disengage adapter ring 26 from body slots 28 thereby permitting its axial movement, the user 79 squeezes body 4 as suggested by arrows 80 in FIG. 7B opposite body slot 28. The appropriate place to squeeze body section 4 is further aided by the provision of three different sets of tactile bumps 82, 83, 84, shown in FIG. 2, opposite body slots 28, 29 and 30. Once body section 4 has been sufficiently deformed to release adapter ring 26, cartridge-needle unit 46 can be moved axially relative to body section 4 from the I.M. injection position of FIG. 6 to the I.V. injection position of FIG. 8, at which adapter ring 26 engages body slots 29. As can be seen in FIG. 8, body slots 29 are positioned so that tip 62 of needle 60 is within interior 10 of body section 4, but near needle end 6. doing so permits syringe assembly 48 to be easily and safely used to inject a liquid into or withdraw a liquid from a membrane valve 86 of a conventional I.V. port 88 as shown in FIG. 8. The opening at needle end 6 is sized to properly guide injector arm 86 while eliminating any substantial possibility of an inadvertent needle stick during such a procedure.

FIG. 9a illustrates the engagement of adapter ring 26 within body slot 29. At FIG. 9B as modified adapter ring 26a is shown with a tapered plunger-facing surface 90. The use of surface 90 keeps adapter ring 26 snug within body slot 29 and also provides a ramp effect to make movement of adapter ring 26a towards plunger end 8 of body section 4 easier.

FIG. 10 illustrates a syringe assembly 48a identical to syringe assembly 48 but with a needle 60a being longer than needle 60. To properly position tip 62 relative to needle end 6, adapter 22 is positioned along body section 4 until adapter ring 26 engages body slots 30 rather than body slots 29.

FIGS. 12a and 11 illustrate further embodiments providing of the proper positioning of tips 62 of needles 60, 60a (the short and long needle versions, respectively). Short needle 670 is used with a conventional width adapter ring 26 as in FIG. 8. However, with syringe assembly 48a, shown in FIG. 11, extra width adapter ring 26b is used. Adapter ring 26b will engage body slots 28a, 29a and 30a but will not engage narrow width body slots 29. However, normal width adapter ring 26 can engage all of the body slots 28a, 29, 29a and 30a. Therefor, adapter ring 26b is repositioned from body slots 28a, past body slots 29 and into engagement with body slots 29a so to properly position tip 62. With syringe assembly 48c, shown in FIG. 12, adapter ring 26 is initially positioned within body slots 29a (although somewhat loosely). Movement of adapter ring 26 from body slot 28a towards plunger end 8 allows adapter ring 26 to engage body slots 29 and thus properly position tip 62 in this case as well. FIG. 12b shows the use of an I.V. drip visual indicator 91 between body slots 29, 29a to show the user which body slot is to be used for use with an I.V. port 88. Other visual indicators or markings could be used adjacent the body slots used for I.M. injections and safe disposal.

Figure 13:
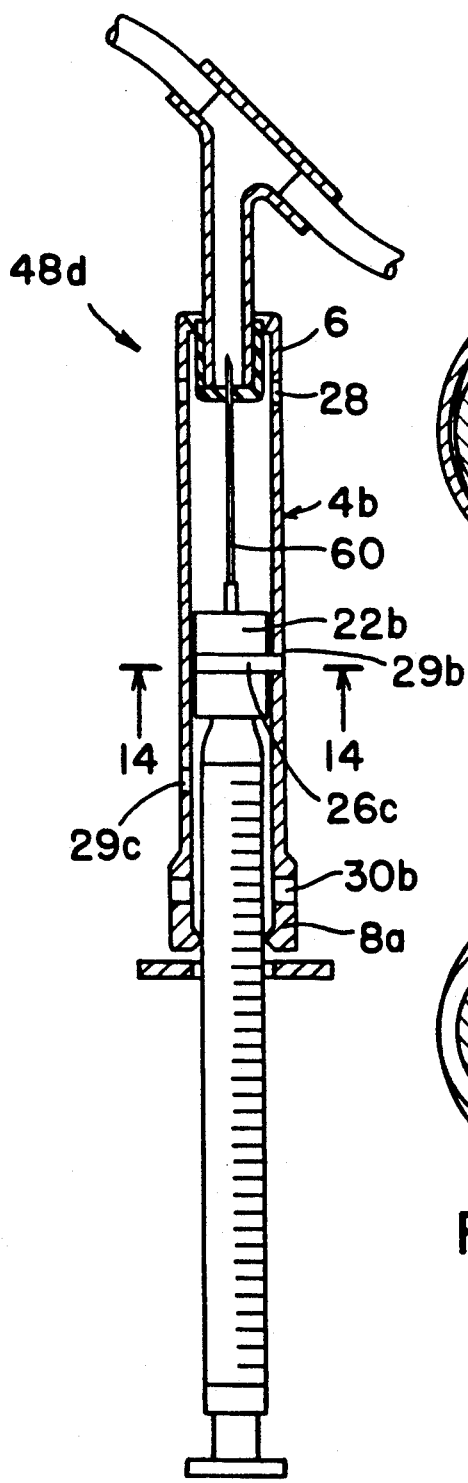
FIGS. 13 and 14 illustrate a further alternative embodiment of the invention in which the adapter ring does not extend completely around the adapter to engage the appropriately positioned body slot for a short needle version of the cartridge needle unit.
Figure 14:
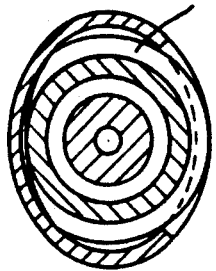
Figure 16:
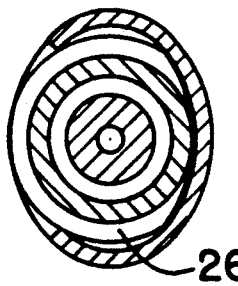
FIGS. 15 and 16 show the embodiment of FIGS. 13 and 14 with a long needle version of the cartridge-needle unit and with an adapter ring positioned to the opposite side of the body section as in the embodiment of FIG. 13, so that the adapter ring of the embodiments of FIGS. 13 and 15 engage the appropriately intermediate disposition body sots located at different axial positions along the body section according to the lengths of the needles.

FIGS. 13–16 illustrate another method by which different length needles can be accommodated, and also demonstrate that adapter ring 26 ned not be a full circle. Syringe assembly 48d, illustrated in FIG. 13, uses a short lengthy needle 60 while syringe assembly 48e uses long length needle 60a while body use a body section 4b. Body section 4b includes a pair of body slots 28, a single body slot 29b, a single body slot 29c and a pair of body slots 30b formed in a plunger end 8a. As can be seen in FIG. 14, adapter ring 26c is generally C-shaped and is sized to substantially impede or prevent rotation of adapter 22b within interior 10 of body section 4b when engaged within the body slot 29b. The axial and rotary position of body slot 29b is chosen to properly position tip 62 of needle 60. Similarly, with reference to FIGS. 15 and 16, adapter 22c has its adapter ring 26d positioned 180° from adapter ring 26c of FIG. 14 so that adapter ring 26d engages body slot 29c rather than slot 29b so tip 612 of needle 60a is also properly positioned relative to needle end 6 of body section 4b.

Figure 15:
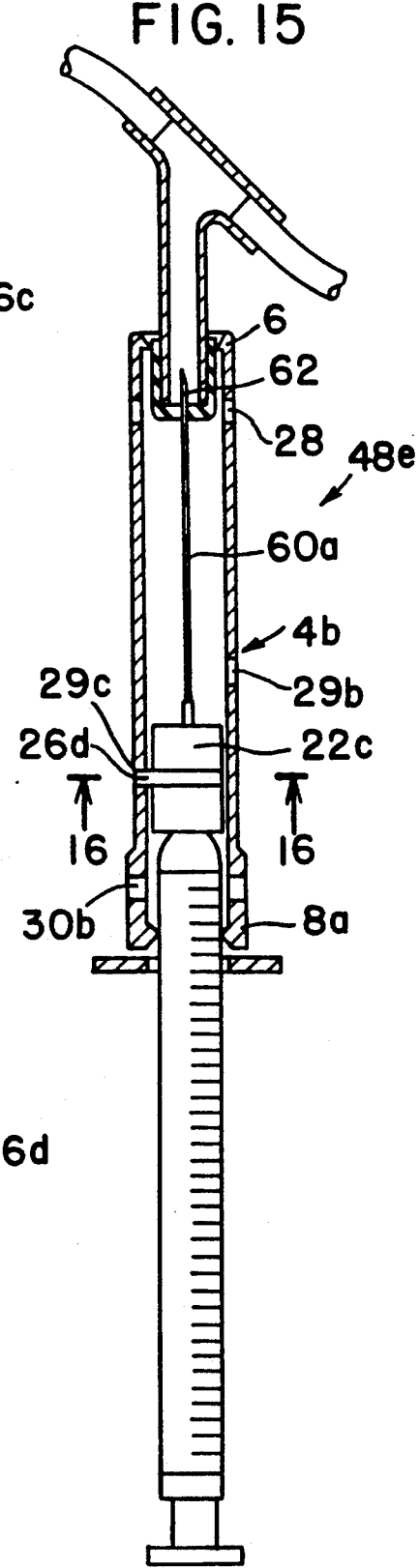

In both embodiments of FIGS. 13 and 15, plunger end 8a is thickened or strengthened. This helps to rigidify body section 4b at body slots 30a so that once adapter rings 26c, 26d enter body slots 30a, it will be quite difficult to squeeze plunger end 8a of body section 4b with sufficient force to disengage the adapter ring from the body slot.

FIGS. 17, 18A and 18B illustrates a situation in which the body slots 28, 29 and 30 are replaced by flanges 92, 93, 94 which engage an annular slot 96 formed in adapter 22d. The disengagement of flanges 92 from slot 96 occurs in the same manner as discussed with reference to FIGS. 7A and 7B. That is, the user squeezes body section 4c as shown by arrows 80 to cause the disengagement of flanges 92 from slot 96. This permits the relative axial movement of adapter 22d within body section 4c so to reposition needle 60 within the interior 10 of the body section.

FIG. 19 illustrates a still further alternative embodiment of the syringe assembly 48 of FIG. 4. Syringe assembly 48f is similar to syringe assembly 48 except that adapter 22 is replaced by providing an adapter ring 26e as an integral part of hub 64a. This eliminates the need for adapter 22, but likely requires modification of a conventional cartridge-needle unit.

Turning now to FIGS. 20 and 21, a syringe assembly 48g is shown adapted for use with a smaller sized cartridge-needle unit 46a. One distinction between syringe assembly 48g and syringe assembly 489 is the use of an extended length adapter 22e, a portion 98 of which extends past finger grips 42 to permit user 70 to grasp portion 98 when placing the assembly into an I.V. injection or a safe disposal condition.

Body section 4c of syringe assembly 48g includes a pair of inwardly biased fingers 100 having protrusions 102 shaped to conform to the outer surface of portion 98 of adapter 22e. This helps to center adapter 22e, and cartridge-needle unit 46a therewith, within interior 10 of body section 4c. Liners 100 could also be used to center and stabilize cartridge-needle unit 46 in the other embodiments.

Other modification and variations can be made to disclosed embodiments without departing from the subject of the invention as defined in the following claims. For example, the invention is particularly adapted for use with a cartridge-needle unit. However, the invention is also adaptable for use with syringes and can be used with separately packaged cartridges nd cartridge-needle units as well. While most of the disclosed embodiments use an elliptically shaped body section, the body section could, however, be another shape, such as generally triangular, as well. The deformation of the body section could also be created by twisting or rotating the adapter ring (or other radially extending member) to cause the radially extending member to disengage from a body slot. However, doing so would require the appropriate rotary manipulation of the pieces in addition to axial manipulation. While enclosure unit 2 is, in the preferred embodiment, a one-piece molded structure, it may be desirable to make it from two or more pieces. For example, it may be desirable to make adapter 22 and cap 16 as separate pieces. Also, it may be desired to mount adapter 22 to hub 64 prior to positioning the cartridge-needle unit within the body section.

What is claimed is:

1. A syringe assembly comprising:
  a syringe structure including a barrel and a removable needle assembly;
  the syringe structure including a first positioning element;
  a hollow body housing at least a portion of the syringe structure;
  the body including an inner surface having a second positioning element formed thereat, the first and second positioning elements sized for mating engagement when aligned so to prevent relative axial movement of the body and the syringe structure, and
  the body including means for permitting at least a part of the body to be deformed radially to disengage the first and second positioning elements to allow relative axial movement of the body and the syringe structure; and
  one of the first and second positioning elements including an effectively circumferential radial projection and the other of the first and second positioning elements including a recess sized to accept at least a portion of the radial projection regardless of the relative rotary orientation of the syringe structure and the body,
  wherein the first positioning element includes said radial projection.

2. The assembly of claim 1 wherein the syringe structure includes a cartridge-needle unit having a barrel, a piston mounted within the barrel, and a needle assembly mounted to the barrel.

3. The assembly of claim 1 wherein the radial projection includes an annular ring.

4. The assembly of claim 1 wherein the body has a substantially constant wall thickness.

5. The assembly of claim 1 wherein the inner surface is generally elliptical in cross-section.

6. The assembly of claim 5 wherein the outer surface is generally elliptical in cross-section.

7. The assembly of claim 5 wherein the body deformation permitting means includes the body constructed to be resilient and sufficiently deflectable through the application of a squeezing force by a user so to temporarily change the cross-sectional shape of the inner surface at the second positioning element form generally elliptical to generally circular thus releasing the first and second positioning elements.

8. The assembly of claim 1 wherein the recess includes a circumferentially extending slot formed through the body.

9. The assembly of claim 1 wherein the inner surface of the body includes a plurality of axially spaced-apart recesses.

10. The assembly of claim 1 wherein the body of one said assembly is frangible connected to the body of at least one other said assembly to comprise a set of said assemblies.

11. The site of claim 10 wherein the assemblies have longitudinal axes, the longitudinal axes of the assemblies being parallel.

12. A syringe assembly comprising:
  a syringe structure;
  the syringe structure including a first positioning element;
  a hollow body housing at least a portion of the syringe structure;
  the body including an inner surface having a second positioning element formed thereat, the first and second positioning elements sized for mating engagement when aligned so to prevent relative axial movement of the body and the syringe structure;
  the body including means for permitting at least a part of the body to be deformed radially to disengage the first and second positioning elements to allow relative axial movement of the body and the syringe structure; and
  one of the first and second positioning elements including an effectively circumferential radial projection and the other of the first and second positioning elements including a recess sized to accept at least a portion of the radial projection regardless of the relative rotary orientation of the syringe structure and the body
  wherein the syringe structure includes a cartridge-needle unit having a barrel, a piston mounted within the barrel, and a needle assembly mounted to the barrel and an adapter mounted to the cartridge-needle unit, the adapter including the first positioning member.

13. A syringe assembly comprising:
  a syringe structure having a radially extending ring, said syringe structure including a needle, the needle having a needle tip;
  a hollow body housing at least a portion of the syringe structure;
  the body including a generally elliptically-shaped inner surface having first and second axially spaced-apart recesses formed thereat, the recess and ring sized for mating engagement when aligned so to prevent relative axial movement of the body and the syringe structure;
  the recess and ring configured to permit engagement thereof when axially aligned regardless of their relative rotary orientations;
  the first recess positioned so that the needle tip is external of the body when the ring is engaged therewith, the second recess positioned so that the needle tip is within the body when the ring is engaged therewith; and
  the body being constructed to bear resilient and sufficiently deflectable through the application of a squeezing force by a user so to temporarily change the cross-sectional shape of the inner surface from generally elliptical to generally circular thus releasing the ring to allow relative axial movement of the body and the syringe structure.

14. A disposable medical needle apparatus, for use in combination with a needle assembly of the type including an effectively circumferential radial projection, said combination comprising: a case having an elongated cavity surrounded by a longitudinally extending wall, the cavity having a first open end at a first longitudinal end of the wall and having a second open end at a second opposite longitudinal end of the walk, the case having a needle-passing opening in the second end, the case having a recess formed within the interior of the wall sized to accept the radial projection, the radial projection and the recess configured to permit their engagement when axially aligned regardless of their relative rotary reorientations, the case including means for permitting at least a part of the body section to be deformed radially when the radial projection is to be removed from the recess to allow the needle assembly, after use, to be withdrawn from the needle-passing opening and held within the cavity.

15. The apparatus of claim 14 further comprising a needle assembly, having an elongated tubular needle with a sharp distal end, a barrel and a hub, the hub securing the tubular needle the hub to the barrel, the hub having an outwardly extending flange which acts as the radial projection.

16. A self-resheathing safety needle comprising: a longitudinally extending case having a first open end and a second open end and having a wall extending between the first and second ends thereby forming a cavity, a recess extending outwardly from the cavity, a needle assembly having an elongated needle, a barrel and a hub mounting the needle to the barrel, the hub having an effectively circumferential radially extending connector for cooperating with the recess to releasably hold the hub in the case, thereby preventing outward egress of the needle assembly from the cavity through the first end of the case, the connector and the recess configured to permit engagement thereof when axially aligned regardless of their relative rotary orientations, and means for permitting the case to be deformed radially to allow the connector to be withdrawn from eh recess to permit the needle assembly to move along within the cavity.

17. The needle of claim 16 including first and second of said recesses, the first recess positioned so that a portion of the needle is external of the cavity when the connector is engaged therewith, the second recess positioned so that the needle is entirely within the cavity when the connector is engaged therewith.

18. A disposable medical needle protection apparatus comprising:
a tubular outer case having first and second open ends;
a hub axially movable within the case between first and second positions which are proximate the first and second ends, respectively, the hub being adapted to mount a needle which extends past the first and end when the tube is in the first position and which is wholly disposed within the case when the hub is in the second position;
locking means for securing the hub and the needle therewith to the case when the hub is in the first and second positions regardless of the relative rotary orientations of the hub and the case;
release means operable by applying a force to the case for releasing the locking means to permit axial movement of the hub between the first and second positions;
wherein the force applied to the release means is applied tin a generally radial direction of the case and further including means, proximate the second end of the case, for inhibiting the application of the radial force to discourage releasing the locking means after the hub has been retracted to the second position
whereby, following the use of the needle, it can be retracted wholly within the case by activating the release means and moving the hub of the second position to prevent accidental needle stick.

19. Apparatus according to claim 18, wherein the inhibiting means comprises a flange affixed to the case adjacent the second case end and projecting generally radially outwardly therefrom.

20. Apparatus according to claim 18, wherein the release means is defined by a tubular wall of the case dimensioned so that a first portion of the wall extends generally radially beyond a periphery of the hub and a second portion of the wall is in contact with the hub to permit relative movements in a radial direction between the hub and the wall when the force is applied to the wall.

21. Apparatus according to claim 20, wherein the wall and the hub define at least one projection and a cooperating slit oriented transverse to an axis of the case, at least one of which is proximate the second end of the case, the projection and the slit being arranged and dimensioned so that they engage each other when in alignment and thereby lock the hub of the case when the hub is in the second position, and so that the locking means is released by applying the force in a generally radially inward direction to the first portion of the wall.

22. A disposable medical needle protection apparatus comprising:
a tubular outer case having first and second ends;
a hub longitudinally movably disposed within the case and movable between first and second positions proximate the first and second ends of the case, the hub being adapted to firmly hold a needle projecting from the hub in the direction of the first end so that the needle extends past the list end when the hub is in the first position and is wholly disposed within the case when the hub is in the second position; and
releasable locking means defined by the case and the hub including first means for securing the hub of the case when the hub is in either the first or second position, regardless of the relative rotary orientations of the case and the hub, and preventing relative longitudinal movements of the hub in the case, and second means, operable by applying a generally radially directed force to an exterior of the casing, for disengaging the first means to permit relative longitudinal movements of the hub in the casing between the first and second positions
wherein the first means includes means for securing the hub to the case at a third position intermediate the first and second position, and wherein the second means is operable to disengage the hub from the case when it is in the third position to permit movement of the hub from the third to the second position.

23. A disposal medical needle protection apparatus comprising:

a tubular outer case having first and second ends a longitudinal axis and an interior space which, in cross-sectional dimension, has generally transverse major and minor dimensions, the case being constructed of a resiliently deformable material;

a generally cylindrical hub longitudinally movably disposed in the space for movement between first and second positions proximate the first and second ends of the case, the hub being adapted to securely hold a needle projecting form an end thereof so that the needle extends past the first end of the case when the hub is in the first position and is wholly disposed within the space when eh hub is in the second position, the hub having a cross-sectional dimension perpendicular to the longitudinal axis of the case which is less than the major dimension of the space and such that a portion of the hub is normally in contact with a portion of the case defining the minor dimension while a remainder of the hub is spaced from another portion of the case defining the major dimension;

releasable locking means on the hub and the case defined by recesses oriented transversely to the longitudinal axis of the case and effectively circumferential projections formed to be extendible into at least a portion of the recesses regardless of the relative rotary orientations of the hub and the case, there being at least one each of the recesses and the projections; and one of the hub and the case includes the recess and the other of the hub or case includes the projection;

whereby the locking means is released to enable movement of the hub between the first and second positions by manually compressing the case in the direction of the major dimension of the space to thereby reduce the major dimension and correspondingly increase the minor dimension of the space and disengage the projection from the corresponding recess.

24. Apparatus according to claim 23 wherein there are at least three of at least one of the projections and the slits formed in the case, the third one thereof being located intermediate the first and second positions whereby the hub can be locked to the case in a third, intermediate position.

25. A disposable medical needle protection apparatus comprising:

a generally oval, resiliently deformable outer case having first and second ends, a longitudinal axial and first and second slits formed in a portion of the case corresponding to the shorter axis of the oval, such portion being the relatively narrower portion as compared to a portion corresponding to the longer axis of the over which is the relatively wider portion, oriented transversely to the longitudinal axis and located proximate the first and second ends of the case;

a generally cylindrical hub adapted to securely hold a needle projecting from an end thereof, the hub having a diameter selected so that the hub is in contact with the relatively narrower portion of the case and spaced from a relatively wider portion of the case, the hub further including a radially oriented projection adopted to be at least partially received within the slits in the case regardless of the relative rotary orientations of the hub and the case;

the slits and the projection being arranged so that the needle extends past the first end of the case when the projection engages at least a portion of the slit proximate the first end, and so that the needle is wholly disposed within the case and cannot be contacted from an exterior thereof when the projection engages at least a portion of the slit adjacent the second end of the case;

whereby following use of the needle it can be wholly retracted inside the case by applying external pressure to the relatively wider portion of the case adjacent the first end which correspondingly spreads apart the relatively narrower portion of the case and causes disengagement of the projection from the slit so that, thereafter, the hub can be axially moved towards the second end until the projection engages at least a portion of the slit adjacent the second end of the case.

26. Apparatus according to claim 25 including means defined by the case proximate the first end preventing axial movement of the hub past the first end.

27. Apparatus according to claim 25 wherein the hub has a generally tubular configuration and includes first and second, axially oriented apertures, a needle holder including the needle and means on the hub engageable with the holder for substantially immovably securing the holder to the hub.

28. Apparatus according to claim 27 wherein the needle holder includes means or connecting it with an end of a syringe insertable into the case.

29. Apparatus according to claim 28 wherein the connecting means includes means for disengaging the syringe from the needle holder.

30. Apparatus according to claim 28 wherein the case has a length so that an end of the syringe projects past the second end of the case when the projection of the hub engages the slit in the case adjacent the first end thereof, whereby the hub an be moved from adjacent the first end to adjacent the second end by compressing the relatively wider portion of the case and pulling the projecting end of the syringe out of the case.

31. A syringe assembly comprising:

a syringe structure;

the syringe structure including a first positioning element;

a hollow body housing at least a portion of the syringe structure;

the body including an inner surface having a second positioning element formed thereat, the first and second positioning elements sized for mating engagement when aligned so to prevent relative axial movement of the body and the syringe structure;

the body including means for permitting at least a part of the body to be deformed radially to disengage the first and second positioning elements to allow relative axial movement of the body and the syringe structure;

one of the first and second positioning elements including an effectively circumferential radial projection and the other of the first and second positioning elements including a recess sized to accept at least a portion of the radial projection regardless of the relative rotary orientation of the syringe structure and the body;

wherein the body of none said assembly is frangibly connected to the body of at least one other said assembly to comprise a set of assemblies;

the assemblies having longitudinal axes, the longitudinal axes of the assemblies being parallel and the hollow bodies of said set define enclosure units completely housing said syringe structures.

32. The set of claim 31 wherein the enclosure units function as packaging, for shipping and storage, as drug delivery containers, and as sharps containers.

33. A syringe assembly comprising:

a syringe structure;

the syringe structure including a first positioning element;

a hollow body housing at least a portion of the syringe structure;

the body including an inner surface having a second positioning element formed thereat, the first and second positioning elements sized for mating engagement when aligned so to prevent relative axial movement of the body and the syringe structure;

the body including means for permitting at least a part of the body to be deformed radially to disengage the first and second positioning elements to allow relative axial movement of the body and the syringe structure;

one of the first and second positioning elements including an effectively circumferential radial projection and the other of the first and second positioning elements including a recess size to accept at least a portion of the radial projection regardless of the relative rotary reorientation of the syringe structure and the body;

the syringe structure including a cartridge-needle unit having a barrel, a piston mounted within the barrel, and a needle assembly mounted to the barrel; and wherein the body defines an enclosure unit totally enclosing the syringe structure therein.

34. The assembly of claim 33 wherein the enclosure unit is a shipping container.

35. The assembly of claim 33 wherein the enclosure unit functions as a shipping container, a syringe holder and an individual sharps container.

* * * * *